United States Patent
Patel

(10) Patent No.: US 10,357,158 B2
(45) Date of Patent: Jul. 23, 2019

(54) SYSTEM AND METHOD FOR EXCHANGING DUTY-CYCLE INFORMATION IN WIRELESS NETWORKS

(75) Inventor: Maulin Dahyabhai Patel, Tuckahoe, NY (US)

(73) Assignee: KONINKLIJKE PHILIPS ELECTRONICS N.V., Eindhoven (NL)

(*) Notice: Subject to any disclaimer, the term of this patent is extended or adjusted under 35 U.S.C. 154(b) by 1691 days.

(21) Appl. No.: 13/883,768

(22) PCT Filed: Nov. 3, 2011

(86) PCT No.: PCT/IB2011/054896
§ 371 (c)(1),
(2), (4) Date: May 7, 2013

(87) PCT Pub. No.: WO2012/063172
PCT Pub. Date: May 18, 2012

(65) Prior Publication Data
US 2013/0237777 A1    Sep. 12, 2013

Related U.S. Application Data

(60) Provisional application No. 61/410,989, filed on Nov. 8, 2010.

(51) Int. Cl.
*A61B 5/00*    (2006.01)
*A61B 5/0205*    (2006.01)
(Continued)

(52) U.S. Cl.
CPC ........ *A61B 5/0024* (2013.01); *A61B 5/02055* (2013.01); *H04B 13/005* (2013.01);
(Continued)

(58) Field of Classification Search
CPC . A61B 5/0024; A61B 5/02055; A61B 5/7232; A61B 2560/0266; A61B 5/0015;
(Continued)

(56) References Cited

U.S. PATENT DOCUMENTS 5,342,408 A * 8/1994 deCoriolis ......... A61N 1/37276
                                                    607/32
6,216,038 B1    4/2001 Hartlaub
(Continued)

FOREIGN PATENT DOCUMENTS

EP    2227065 A1    9/2010
KR    20100076414 A    7/2010
(Continued)

OTHER PUBLICATIONS

Jurdak, R., et al.; State-Driven Energy Optimization in Wireless Sensor Networks; 2005; IEEE Proc. of 2005 Systems communications; 8 pages.
(Continued)

*Primary Examiner* — Timothy J Neal
*Assistant Examiner* — Jae Woo

(57) ABSTRACT

A wireless medical device (12) includes at least one sensor (14, 18, 22) which monitors physiological data of a patient or an actuator (26) which delivers therapy to the patient. A wireless transceiver (40) transmits and receives information packets related to at least one of the monitored physiological data and the delivered therapy. The wireless transceiver (40) has a duty-cycle limit. The duty-cycle module (50) determines the duty-cycle parameters for the wireless transceiver (40) according to the duty-cycle limit. A communication module (60) controls the transceiver (40) to broadcast at least one duty-cycle parameter when transmitting an information packet or when acknowledging receiving an information packet from a neighboring wireless medical device.

18 Claims, 4 Drawing Sheets

(51) Int. Cl.
*H04B 13/00* (2006.01)
*A61B 5/021* (2006.01)
*A61B 5/024* (2006.01)

(52) U.S. Cl.
CPC ........... *A61B 5/021* (2013.01); *A61B 5/02438* (2013.01); *A61B 5/7232* (2013.01); *A61B 2560/0266* (2013.01)

(58) Field of Classification Search
CPC .......... A61B 2560/0209; H04B 13/005; A61N 1/37252; A61N 1/37276
USPC ........................................................ 600/301
See application file for complete search history.

(56) References Cited

U.S. PATENT DOCUMENTS

| | | | | |
|---|---|---|---|---|
| 6,745,078 B1* | 6/2004 | Buchner | ............... | A61N 1/326 607/72 |
| 6,950,404 B2* | 9/2005 | Pearl | ............... | H04B 1/036 370/252 |
| 6,972,692 B2* | 12/2005 | Eaton | ............... | H04B 1/3838 340/870.07 |
| 6,993,393 B2* | 1/2006 | Von Arx | ............... | A61N 1/08 607/60 |
| 7,375,311 B2* | 5/2008 | Wiklof | ............... | G01N 21/6408 250/201.3 |
| 7,480,490 B2 | 1/2009 | Haartsen | | |
| 7,738,433 B2* | 6/2010 | Tao | ............... | H04W 16/14 370/328 |
| 7,765,425 B1* | 7/2010 | Searles | ............... | G06F 1/10 713/401 |
| 8,024,043 B2* | 9/2011 | Bange | ............... | A61N 1/37223 607/32 |
| 8,055,350 B2* | 11/2011 | Roberts | ............... | A61N 1/37223 607/30 |
| 8,744,519 B2* | 6/2014 | Gandhi | ............... | G06F 9/526 455/500 |
| 8,926,509 B2* | 1/2015 | Magar | ............... | 340/539.12 |
| 2002/0089864 A1* | 7/2002 | Kalman | ............... | H02M 7/4826 363/34 |
| 2002/0136174 A1* | 9/2002 | Gleeson | ............... | H04W 52/283 370/329 |
| 2003/0228875 A1* | 12/2003 | Alapuranen | ............... | H04W 52/225 455/522 |
| 2006/0067245 A1* | 3/2006 | Pearl | ............... | H04B 1/036 370/252 |
| 2006/0120302 A1 | 6/2006 | Poncini et al. | | |
| 2006/0285579 A1 | 12/2006 | Rhee et al. | | |
| 2009/0163781 A1* | 6/2009 | Say | ............... | A61M 5/1723 600/301 |
| 2010/0305414 A1* | 12/2010 | Koo | ............... | A61B 5/0002 600/301 |
| 2011/0066211 A1* | 3/2011 | Von Arx | ............... | A61N 1/37223 607/60 |
| 2011/0176465 A1* | 7/2011 | Panta | ............... | H04W 52/0235 370/311 |
| 2012/0039215 A1* | 2/2012 | Seok | ............... | A61B 5/0024 370/254 |

FOREIGN PATENT DOCUMENTS

| | | |
|---|---|---|
| WO | 2010100014 | 9/2010 |
| WO | 2010100446 | 9/2010 |
| WO | 2010126323 | 11/2010 |

OTHER PUBLICATIONS

Lin, P., et al.; Medium Access Control with a Dynamic Duty Cycle for Sensor Networks; 2004; IEEE Proc. of the Wireless Communications and Networking Conf.; vol. 3; pp. 1534-1536.

Ye, W., et al.; An Energy-Efficient MAC Protocol for Wireless Sensor Networks; 2002; Proceedings IEEE INFOCOM; vol. 3; 1567-1576.

* cited by examiner

SYSTEM AND METHOD FOR EXCHANGING DUTY-CYCLE INFORMATION IN WIRELESS NETWORKS

CROSS REFERENCE TO RELATED APPLICATIONS

This application is a national filing of PCT application Serial No. PCT/IB2011/054896, filed Nov. 3, 2011, published as WO 2012/063172 A1 on May 18, 2012, which claims the benefit of U.S. provisional application Ser. No. 61/410,989 filed Nov. 8, 2010, which is incorporated herein by reference.

DESCRIPTION

The present application relates to wireless devices. In particular, it relates to wireless sensor networks, such as body area networks (BANs) or patient area networks (PANs), which monitor a patient's physiological parameter and transmit a data regarding the sensed parameters to a control system.

Patients have traditionally been monitored using sensing units connected by wires to a base station. These wires inhibited the patient mobility and were labor intensive to install. To improve patient mobility, facilitate installation, and eliminate wire clutter, wireless sensing units have been developed. Certain patients require continuous monitoring of physiological parameters, such as ECG, $SpO_2$, blood pressure, blood sugar, or the like. Though well enough to move about the community, they were restricted to a hospital room, the hospital ward, a convalescent room, or their home to facilitate continuous monitoring of physiological parameters. To venture out of these areas, the patients would be unmonitored.

In order to continuously monitor patient physiological parameters without constraining their activities, it is desirable to be able to mount sensors on the body of the patient, which are light and compact as possible while also being capable of communicating wirelessly with each other and a base station. A body area network (BAN) includes multiple nodes which are typically sensors that can be either wearable or implantable in to the human body. The nodes monitor vital body parameters and/or movements, and communicate with each other over a wireless medium. The nodes can transmit physiological data from a body to a control unit from which the data can be forwarded, in real-time, to a hospital, clinic, or elsewhere over a local area network (LAN), wide area network (WAN), a cellular network, or the like.

The requirements for designing BANs include energy efficiency of the nodes while adhering to geopolitical regulatory requirements regarding the use of the radio spectrum. In the United States, the Federal Communication Commission (FCC) divides the communication frequency spectrum into many bands that have been allocated, leased or sold to specific users/industries (e.g. radio, television, satellite, cellular, etc.). The FCC sets and monitors the compliance with technical requirements in response to the increasing demand for spectrum access. Imposed restrictions include frequency band, bandwidth, duty-cycle limitations, maximum transmit power limitations, specific absorption rate, or the like.

To facilitate wireless medical devices, the FCC has allocated 401-406 MHz frequency band for Medical Device Radiocommunication (MedRadio) Service on a shared, secondary and non-interference basis. MedRadio bands are intended to be used for ultra-low power wireless communications involving implanted and body-worn medical devices used for diagnostic and therapeutic functions. Examples of medical devices implanted in human body that may use MedRadio bands for communication are cardiac defibrillators, pacemakers, nerve/brain stimulators, implanted drug pumps, or the like. Body-worn devices such as ECG, EMG, EEG and hearing aids may also use MedRadio bands for wireless communication.

The FCC has mandated that the transmission duty-cycle of MedRadio devices operating in either the 401-402 MHz or 405-406 MHz bands should not exceed 0.1% based on the total transmission time during a one-hour interval. The duty-cycle is defined as the ratio, expressed as a percentage, of the maximum transmitter "ON" time on one or more carrier frequencies, relative to a one hour period. In Europe, several other allocated bands have duty-cycle restrictions. For example, the industrial, scientific and medical (ISM) bands operating in the 433.05-434.79 MHz range has a duty-cycle restriction of 10%, the 868-868.6 MHz band has a duty-cycle restriction of 1%, and the 868.7-869.3 MHz band has a duty-cycle restriction of 0.1%.

Recently, the FCC has issued a notice of proposed rule making to allow shared secondary usage of 2.36-2.40 GHz band for wireless Medical Body Area Networks (MBANs), FCC Notice of Proposed Rulemaking 09-57, June 2009. The MBANs are intended to support on-body medical devices used for diagnostic and therapeutic applications. In the notice, the FCC has sought to restrict the maximum duty-cycle of devices operating in MBANs to 25%.

In a typical communication session, e.g. using IEEE 802.11b MAC protocol, the sender transmits a Request to Send (RTS) message to a receiver. Upon reception of the RTS message, the receiver transmits a Clear to Send (CTS) message which silences other wireless nodes in its vicinity and enables the sender of the RTS message to begin data transfer. Upon receiving the CTS message, the sender transmits the data and upon error-free reception of the data the receiver transmits an Acknowledgement (ACK) message.

For each transmitter, it is straightforward to track its current duty-cycle, to suspend transmissions when the duty-cycle reaches the maximum limit, and to resume transmissions when the duty-cycle is within the acceptable limits. However, the sender may not be aware of the current duty-cycle of its intended receiver. The intended receiver may be inhibited from responding to the sender with a CTS or ACK message because the receiver has reached its duty-cycle limit. The sender may incorrectly conclude that the message has collided, the received message has errors, the receiver is out of range, the receiver is dead (i.e. battery depleted), the receiver is sleeping, or the like. The sender may retransmit the message or listen idly in anticipation of an incoming message. Consequently, the sender wastes valuable energy, bandwidth, duty-cycle, resources, and the like. For at least the shortcomings described above, it would be therefore advantageous to provide a solution for exchanging duty-cycle information between devices to support the requirements of applications.

The present application provides a new and improved system and method for exchanging duty-cycle information in wireless body area networks which overcomes the above-referenced problems and others.

In accordance with one aspect, a wireless medical device is presented. The wireless medical device comprises at least one of a sensor and an actuator. The sensor monitors physiological data of a patient while the actuator delivers therapy to the patient. The device includes a wireless transceiver which transmits and/or receives control packets (e.g.

beacons) and/or information packets related to at least one of the monitored physiological data and delivered therapy. The wireless transceiver has to comply with predetermined duty-cycle limits which define a maximum transmission "ON" time within a predefined time window. A duty-cycle module determines duty-cycle parameters of the wireless transceiver according to the duty-cycle limit. A communication module controls the transceiver to broadcasts, unicast, and/or multicast at least one duty-cycle parameter when transmitting a control packet or an information packet or when acknowledging reception of an information packet from a neighboring wireless medical device.

In accordance with another aspect, a method for wirelessly transmitting medical information is presented. The method includes at least one of a monitoring physiological data of a patient and delivering therapy to the patient. Information packets related to at least one of the monitored physiological data and delivered therapy are wirelessly transmitted and/or received. The wireless transmission has a duty-cycle limit which defines a maximum transmission "on" time during a predefined time window. Duty-cycle related parameters of the wireless transmission are determined according to the duty-cycle limit. At least one duty-cycle parameter is broadcasted, unicasted, and/or multicasted when transmitting an information packet or control packet or when acknowledging receiving an information packet from a neighboring wireless medical device.

One advantage resides in improved regulatory compliance.

Another advantage resides in optimizing the transmission of critical medical information.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
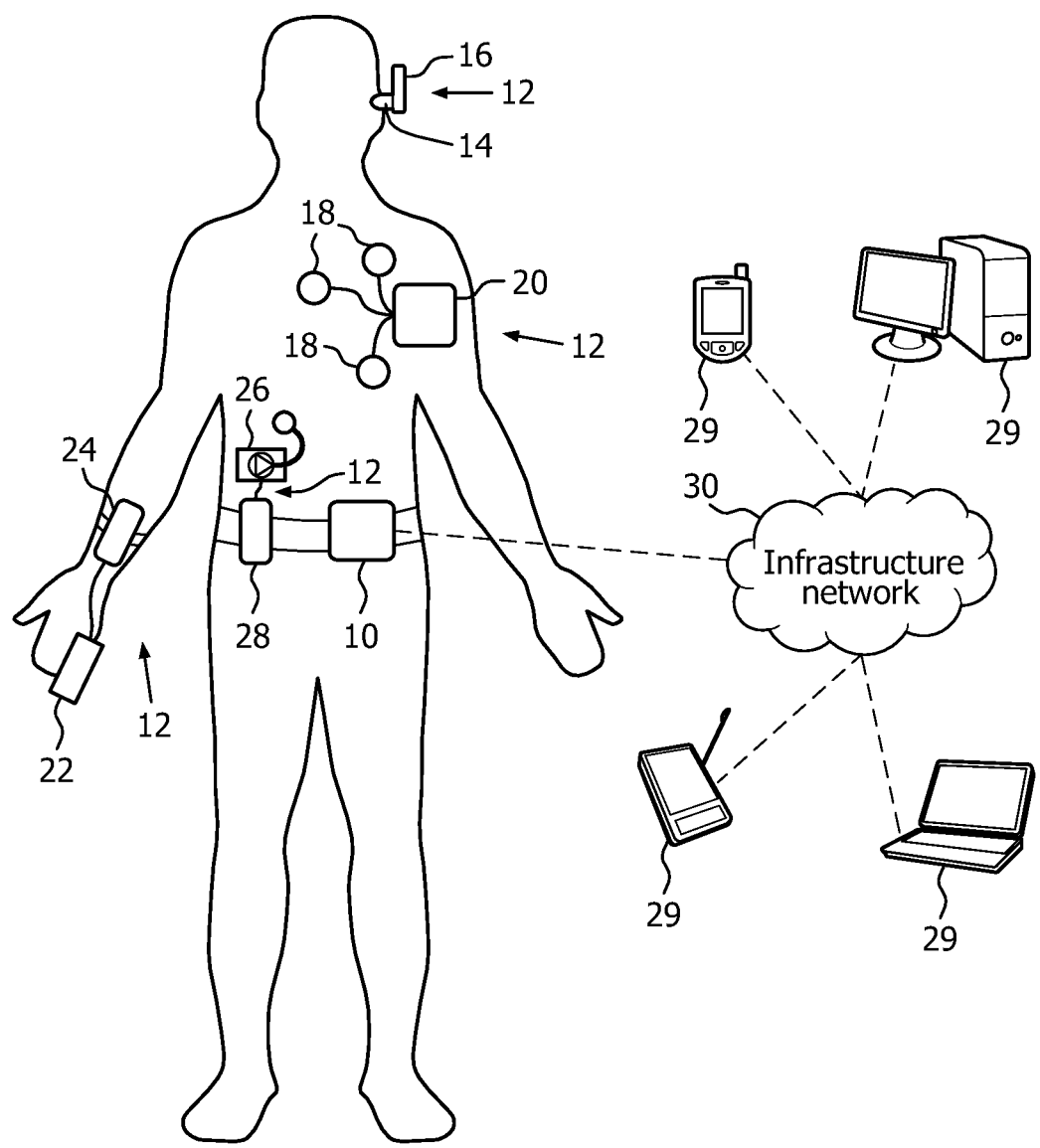
FIG. 1 is a diagrammatic illustration of a medical wireless network.

With reference to FIG. 1, a plurality of wireless medical devices includes a hub medical device 10 and a plurality of wireless medical devices 12 arranged approximate to a patient's body for monitoring and recording various physiological parameters, administering therapy, or the like. The wireless medical devices 12 communicate wirelessly to the hub medical device 10. Various wireless medical devices are contemplated, such as an inner-ear sensor 14 connected to an associated electronic module 16 which is disposed at least partially in the patient's ear to measure temperature, blood pressure, pulse rate, or the like. As another example, the wireless medical devices 12 can include an ECG monitor having a plurality of ECG sensors or electrodes 18 connected to an electronic module 20 which measures and interprets the sensed signals. As another example, an $SpO_2$ sensor 22 senses blood oxygen and pulse rate, which are communicated by an associated electronics module 24. As another example, an infusion pump or other actuator 26 injects or otherwise dispenses medications into the patient's body under the control of electrical signals from an associated electrical module 28. Other wireless medical devices 12 which sense physiological parameters or deliver therapy includes pacemakers, hearing aids, vision aids, prosthetic limbs, artificial organs, and the like.

The wireless hub 10 conveys the received signals from the wireless medical devices 12 to other wireless medical devices 29, such as computer workstations, cellular phones, personal digital assistants, tablet computers, and the like, via an infrastructure network 30. Communications between the hub and the wireless network 30 can be via WiFi, via the internet, via cellular network, via relatively high power RF transmissions, or the like. The wireless medical devices 12 and the hub 10 may interact with one another in various configurations. For example, in a star network, each of the wireless medical devices 12 communicates directly with the hub medical device 10. The hub device receives acknowledgment packets or beacon packets from the devices 12 to, for example, synchronize the devices in anticipation of sending and receiving information packets, control signals, and the like, from the hub 10. In a mesh network, the devices 12 communicate directly with each other and the hub 10. Some of the devices 12 may communicate directly with the hub 10, may communicate indirectly with the hub via other devices, such as computers, PDA's, mobile phones, or the like. These other devices may communicate directly with the wireless medical devices 29 or indirectly via the infrastructure network 30 rather than via the hub 10.

Figure 2:
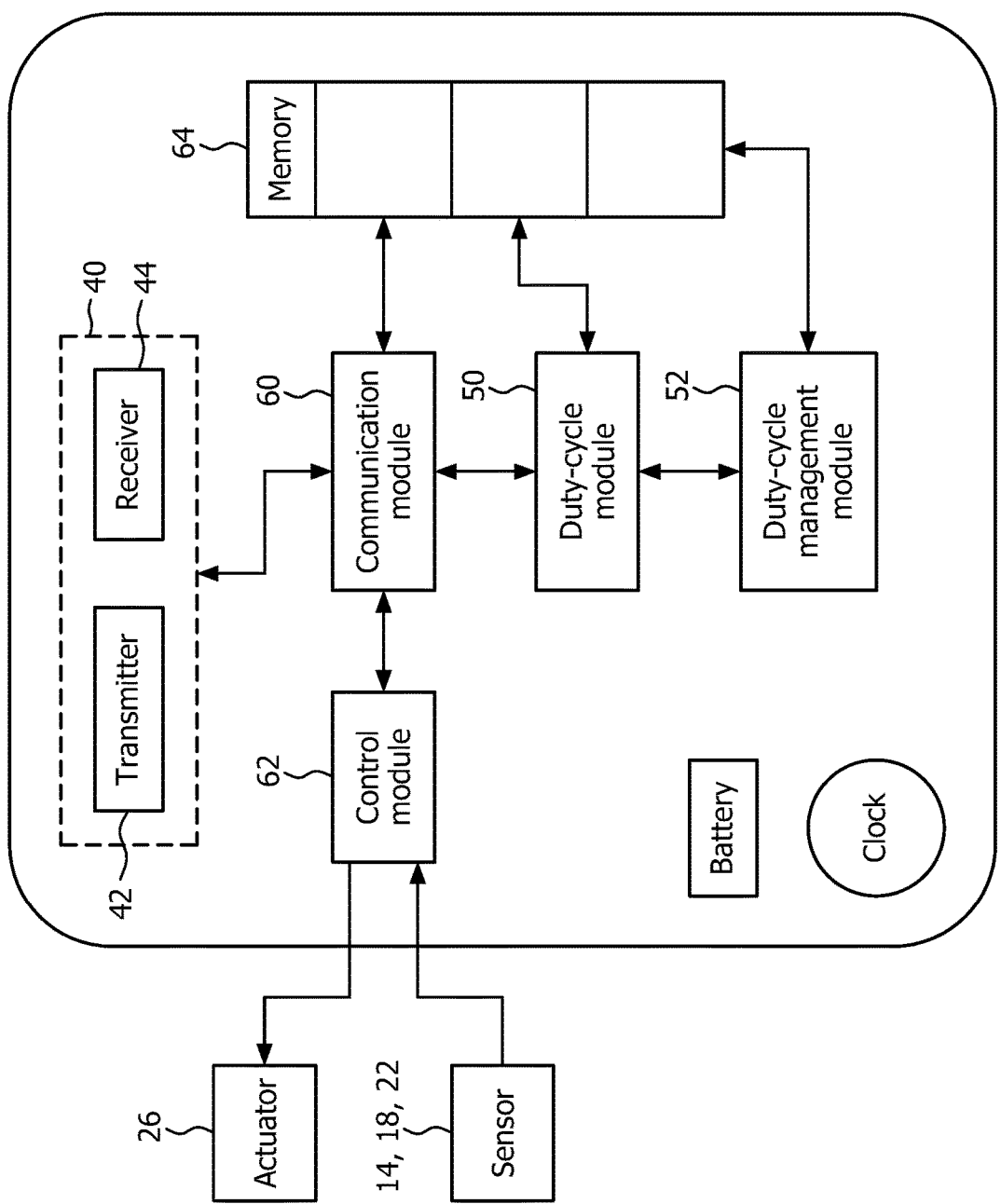
FIG. 2 is a detailed illustration of one of the wireless medical devices of FIG. 1.

With reference to FIG. 2, each wireless medical device 12 includes at least one of a sensor 14, 18, 22, which monitors physiological data of the patient or an actuator 26 which delivers therapy to the patient. The electronics module 20, 24, 28, associated with each sensor, actuator, or combination, includes a wireless transceiver 40 with a transmitter 42 and a receiver 44 which transmit and receive, respectively, information and/or control packets to/from at least one of the neighboring wireless medical device 12 and the wireless hub 10. Each wireless transmitter 42 has a duty cycle limit which limits the transmitter "ON" time relative to a predefined time window. For example, a transmitter may be limited to a duty cycle of 25% over a one hour time window. This restricts the transmitter "ON" time to at most 900 seconds during any 1 hour time window.

A duty-cycle module 50 determines duty-cycle parameters of the wireless transceiver. The duty-cycle parameters include a current transmission duty-cycle which is computed by tracking the amount of time the transmitter is in "ON" state during a current time window, a remaining transmission duty-cycle which defines the available (for use) duty-cycle during the current time window, and an offset of time from current time when sufficient duty-cycle will be available.

A duty-cycle management module 52 determines a transmission mode for the transceiver 40 based on at least one of the current duty-cycle, remaining duty-cycle and time offset parameters of the wireless medical device and those of neighboring wireless medical devices. The transmission mode includes a fragmentation mode which fragments the information packets across a plurality of time windows such that the duty-cycle limit is not exceeded in a current time window. In a modulation mode, at least one of frequency and amplitude modulation parameters of the transceiver 40 are adjusted to reduce a transmission time of the packet such that the duty-cycle limit is not exceeded in a current time window. In a compression mode, the information packet is compressed to reduce the transmission time of the packet such that the duty-cycle limit is not exceeded in a current time window. In a delay mode, the transmission of the packet is delayed to a subsequent time window such that the duty-cycle limit is not exceeded in the current time window. In an aggregation mode, smaller packets are aggregated into a larger packet such that the duty-cycle limit is not exceeded in the current time window. In a priority mode, higher priority packets are transmitted in a current time window and lower priority information is transmitted in subsequent time windows such that the duty-cycle limit is not exceeded in the current time window.

A communication module 60 receives physiological information sensed by the sensor 14, 18, 22 via a sensor or actuator control module 62. The control module 62 also communicates with the actuator 26 to control its operation in accordance with received information packets. The communication module packages the sensed information and other transmission information such as acknowledgments, and the like, into information packets. The communication module controls the transceiver to transmit the packets with a duty-cycle dictated by the duty-cycle module 50 and the duty-cycle management module 52.

A memory 64 stores information for later transmission, information about other wireless medical devices in the body area network, such as remaining duty-cycle, and the like. For example, when other wireless medical devices have reached or are nearing their duty-cycle limit, they may cease to send acknowledgments. By keeping track of the remaining duty-cycle of other wireless medical devices, the communication module knows whether acknowledgment signals will be received and type of acknowledgement to be expected, whether modulation or spreading parameters will be changed, whether data will be compressed, how compressed the data may be, whether to expect communications on a different frequency band, a delay in communication and the length of the expected delay, or the like.

Figure 3:
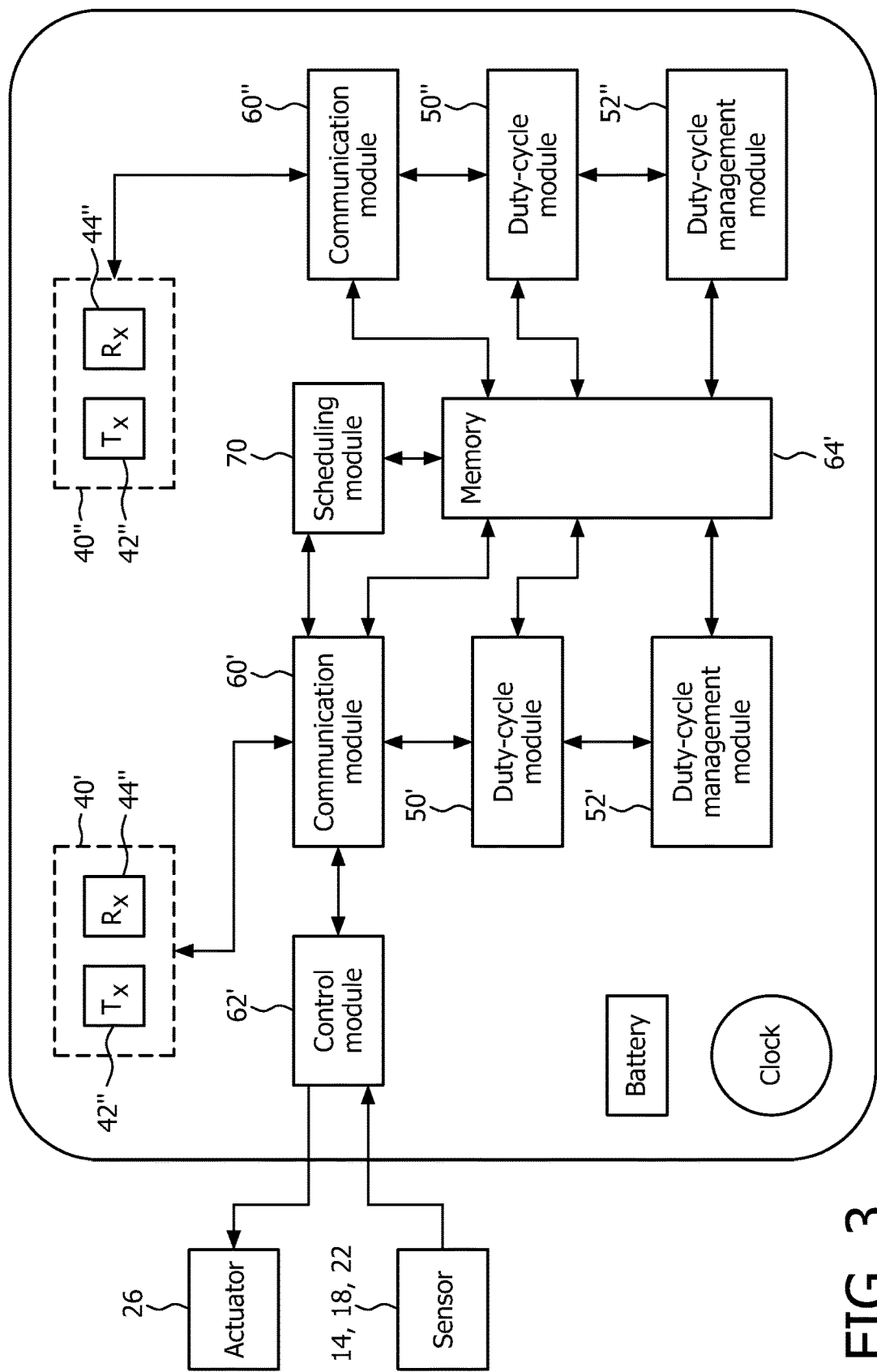
FIG. 3 is a diagrammatic illustration of the hub medical device of FIG. 1.

With reference to FIG. 3, the hub medical device 10 includes a first transceiver 40' which communicates with the other wireless medical devices of the body area network and a second transceiver 40" which communicates with the infrastructure network 30. The wireless hub may be connected with a physiological data sensor and/or an actuator like the other wireless medical devices, or may function merely as a central controller or coordinator and for transferring physiological and/or therapy related information to and from the network 30. For communicating with the other wireless medical devices 12 of the body area network, the wireless hub 10 includes a duty-cycle module 50' which determines the duty-cycle parameters and a duty-cycle management module 52' which determines the transmission mode based on at least one of the current duty-cycle, remaining duty-cycle, and time offset parameters of itself and the other wireless medical devices. A communications module 60' controls the transceiver 40' to broadcast, unicast, and/or multicast at least one duty-cycle parameter when transmitting an information or control packet or when acknowledging receipt of an information packet in a transmission mode as indicated by the duty-cycle module 50' and the duty-cycle management module 52". If the hub unit 10 is connected with a sensor or actuator, then it also includes a sensor or actuator control module 62'.

The wireless hub also includes a scheduling module 70 which schedules timeframes (a.k.a. superframes) of the wireless medical devices 12 according to duty-cycle parameters of the respective wireless medical devices 12. The scheduling module controls the communication module 60' and transceiver 40' to transmit and receive packets in scheduled timeframes to and from the respective wireless medical devices 12. The scheduling module 70 can receive the duty-cycle parameters directly from the communication module 60' or from memory 64'.

The wireless hub 10 also includes a communications module 60" for controlling the transceiver 40" to communicate with the network 30. A duty-cycle module 50" and a duty-cycle management module 52" monitor the duty-cycle with which the transceiver 40" is communicating with the network 30 relative to duty-cycle requirements and controls the duty-cycle accordingly as discussed above.

Figure 4:
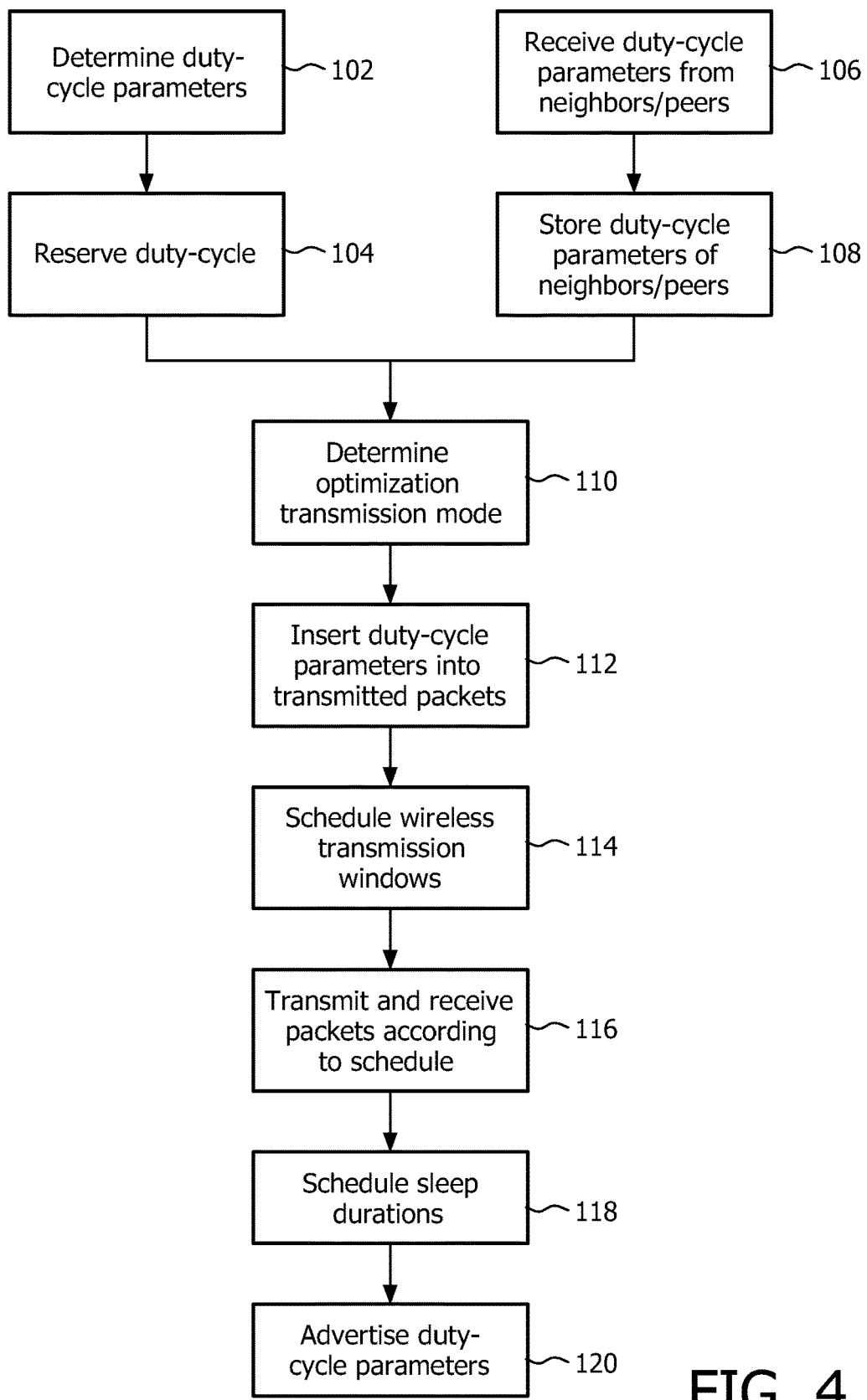
FIG. 4 is a flow chart illustrative of a method of operation.

With reference to FIG. 4, duty-cycle is defined as a percentage of time that the transmitter is in the "ON" state within a predefined window of time, e.g. in the past one hour. Each wireless device computes and tracks its own duty-cycle. The duty-cycle is computed over a sliding window of time by summing durations of the transmitter "ON" time within the window of time and converting the sum into a percentage relative to the duration of the time window. If the transmitter is ON for a total of 3.6 seconds in the past one hour (3600 seconds), then the current duty-cycle is 1%. If the transmitter has been silent for the past hour, then the current duty-cycle is 0%.

The duty cycle can be expressed in bits, symbols, time frames, or in other suitable units. At 102, the duty-cycle parameters such as current duty-cycle, amount of remaining duty-cycle and time offset are calculated. The transmitter tracks the amount of time it spends in the "ON" state within the given time window to compute the duty cycle. In a packet/frame based radio, this can be computed per packet/frame basis just above the PHY layer. Thus, the duty-cycle information is readily available at the MAC layer.

A device might chose not to exhaust its entire transmission "ON" time in one session or with one neighboring device. Rather, the available duty-cycle may be divided among the neighboring devices and/or over multiple communication sessions. Hence, it is useful for the communicating wireless medical device to know how much time is available for the current session with a neighbor. For example, a device reserves 10% of the available time within a predefined window of time interval for communicating data frame transmissions to a neighbor and 5% of the available time for acknowledgments to frames received from that neighbor. Another 10% of the available time, for example, may be allocated for control or management frames, such as beacons. The device reserves the fraction of the duty cycle for intended purposes at 104.

At 106, each receiver receives the duty-cycle information of the neighboring wireless medical devices 12 with which it communicates. At 108, the received duty cycle parameters of neighbors are stored in the memory. The device uses this tracked duty-cycle information in conjunction with its own current duty-cycle to optimize the available transmission times.

At 110, each receiver determines an optimization transmission mode which optimizes transmission efficiency based on the predetermined duty-cycle requirements and the duty cycle information received at 106 from the neighboring wireless medical devices 12.

Various optimization transmission modes include fragmenting the a large packet into smaller packets such that transmitting the smaller packets saves the duty cycle or prevents the duty cycle value to exceed the limit. Another option is for the transmitter to employ a higher order modulation technique, e.g., 16 QAM instead of QAM (or QPSK), to reduce the over-air transmission time such that the duty-cycle is conserved. As another option, the transmission of packet is delayed until a time when the packet transmission would not cause the duty-cycle limit to be exceeded. One optimization transmission mode prioritizes the information to be transmitted. Higher priority information is transmitted first if the duty-cycle is in short supply. Periodic housekeeping control messages are delayed when the duty-cycle is in short supply. If the pending high priority messages cannot be transmitted due to duty-cycle limit restrictions, then the transmitter indicates that it has pending high priority messages for the receiver and the offset time indicative of when transmissions will resume. Thus, the receiver can be ready to receive these messages by waking up at the indicated time and reserving the appropriate duty-cycle for acknowledgments. The duration of the packet can be reduced by stripping the optional control fields from the packet.

Another optimization mode includes a reservation mode in which the hub 10 or wireless medical devices 12 periodically advertise a poll message, or a beacon message, which indicates the amount transmit time is available, e.g., based on the current duty-cycle. In response to the poll or beacon message, the other wireless medical devices 12 may contend to transmit a reservation message to reserve a future timeframe to transmit data. Upcoming time windows are reserved for data transfer among neighboring devices such that duty cycle is not exceeded in the current time window in each of the devices.

Another optimization transmission mode is a compression mode in which the data can be compressed to save transmission time. Furthermore, the data can be aggregated to reduce the transmission time, e.g. instead of transmitting raw data, the data can be aggregated or filtered prior to transmission data. In an encoding mode, the coding scheme of the transmitter 42 is adjusted to encode more information in the current time window such that the duty-cycle limit is not exceeded. For example, when the available duty cycle is abundant then the coding rate of 1/3 can be employed by the transmitter which means fewer information bits and more redundant bits are transmitted. On the other hand when duty cycle is scarce, the coding rate can be adapted to 1/1 to transmit more information bits. A Frame aggregation mode can be employed to combine multiple short frames into one large frame to reduce overhead (i.e. PHY header and/or MAC header) and save duty-cycle.

In an acknowledgement mode, the acknowledgement policy is changed, e.g. from an individual acknowledgment to a cumulative acknowledgement policy, such that the duty-cycle limit is not exceeded in the current time window. For example, when the receiver is running short on remaining duty-cycle, the acknowledgment policy can be changed to a cumulative acknowledgement policy, where multiple received packets are cumulatively acknowledged, or an unacknowledged delivery policy, where received packets are not acknowledged rather than an individual acknowledgement policy where each data message is acknowledged individually. If a potential transmitter knows that the receiver is unable to transmit acknowledgments due to duty-cycle restrictions, then the transmitter delays its transmissions until a time when the receiver is able to acknowledge. Alternately, the transmitter would transmit the messages if it has not exceeded its duty-cycle limit, but it would expect acknowledgments at a later time. The sending device would not resend the transmitted packets in the absence of an acknowledgment for the appropriate duration.

In a retry mode, the retry limit for retransmissions of unacknowledged packets can be varied according to the available duty-cycle such that the duty-cycle limit is not exceeded in the current time window. For example, retransmission attempts can be limited to one attempt instead of up to three or more attempts when duty-cycle is sufficient yet still scarce.

In a spectrum mode, the frequency band of operation is switched to a less restrictive band such that information is transmitted while complying to the regulatory requirements. For example, when a group of the wireless medical devices 12 and/or hub 10 cannot continue packet exchanges due to duty-cycle restrictions, the devices 10, 12 can switch to another channel or frequency band which does not restrict the duty-cycle, or at least is less restrictive of duty-cycle. For example, a pair of medical devices communicating over a 2.36 GHz channel may decide to switch channels to 2.4 GHz ISM when the current duty-cycle approaches the regulatory limit. In the United States, the 2.36 GHz channel has a 25% duty-cycle limit imposed by the FCC; whereas, there is no restriction on duty-cycle in the 2.4 GHz ISM band. Due to the proximity of the 2.4 GHz ISM band and the 2.36 GHz band, the same radio transmitters and receivers can efficiently operate in both bands. In another embodiment, the hub 10 and wireless medical devices 12 includes a plurality of transmitters 42 each tuned to a unique frequency with a corresponding duty-cycle limit which is monitored by the duty-cycle module 50.

In a channel bonding mode, multiple frequency channels are combined to increase the transmission rate of packets such that the duty cycle is not exceeded in the current time window. For example, the duty cycle is conserved by combining multiple frequency channels, such as 2.36 GHz and 2.4 GHz, to increase the transmission rate of packets. The channel bonding mode increases the amount of packet data which can be transmitted within a similar time window.

In a spreading mode, spreading parameters of the transceiver 40 are adjusted to reduce the transmission time of the packet such that the duty-cycle is conserved. For example, in a direct sequence spread spectrum technique, instead of encoding 4 data bits with a pseudonoise (PN) sequence of 32 chips, the transmitter can encode 4 data bits with a PN sequence of 16 chips thereby doubling the data transfer rate.

At 112, the duty-cycle parameters, such as current duty-cycle, amount of remaining duty-cycle, and time offset, are inserted into the packet to be transmitted. In one embodiment, each packet begins with a PHY header followed by an MAC header. The additional duty-cycle related data in the MAC header, or in other suitable locations in the packet, informs the receiver, such as a neighboring wireless medical device or host device, the duration of the sender's transmitter can be in the "ON" state before it is forced to shut off. The current duty-cycle may be calculated assuming successful transmission of the packet on hand. The amount of remaining duty-cycle is indicative of the amount of duty-cycle available for the current communication session, including the entire sequence of packet exchanges.

At 114, transmissions are intelligently scheduled according to the received duty cycle parameters of the devices 10, 12 of the BAN. By knowing the available duty-cycle information of its neighbors, one of the wireless medical devices 10, 12 can intelligently schedule its transmissions to that neighbor. If the neighbor has reached its duty-cycle limit, then transmissions to that neighbor are scheduled for a later time. In one embodiment, the hub device 10 receives and tracks the duty-cycle parameters from all of the wireless medical devices 12 and determines an intelligent schedule for transmissions with the available scheduling module 70. In another embodiment, the wireless medical devices 12 perform the scheduling with the available duty-cycle management module 52.

Before attempting to transmit a packet, the transmitter checks whether transmitting the packet at hand will cause the duty-cycle to exceed the predefined limit. If not, then the packet is transmitted at 116.

The duty-cycle information can be used to schedule a sleep mode 118 where a sender or receiver enters a sleep mode to conserve battery life. If a wireless device 12 is unable to transmit due to available duty-cycle limitations, then it can put itself into a sleep mode until the time when it is allowed to transmit again, thereby saving energy. Alternatively, the hub device 10 can instruct the wireless medical device 12 to enter or schedule a sleep mode.

A frame of time, for example, a beacon period or a superframe, can be predefined according to regulatory requirements and all of the devices are synchronized to this timeframe. At 120, the hub device 10 that communicates with the other wireless medical devices 12 of the body area network periodically advertises a poll message, or a beacon, which indicates the amount transmit time, e.g., based on the current duty-cycle, is available. In response to the poll or beacon message, the other wireless medical devices 12 may contend to transmit a reservation message to reserve a future timeframe to transmit data. During the active portion of the timeframe, the devices may exchange the messages and may reach the duty-cycle limit, causing them to cease further transmission until a new timeframe begins.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A wireless medical device, comprising:
    at least one of a sensor configured to monitor physiological data of a patient and an actuator which delivers therapy to the patient;
    a wireless transceiver configured to transmit and/or receive information packets related to at least one of the monitored physiological data and delivered therapy, the wireless transceiver having a duty-cycle limit;
    a duty-cycle module configured to determine duty-cycle parameters of the wireless transceiver according to the duty-cycle limit, the duty-cycle parameters including at least: a current transmission duty-cycle which defines the duty-cycle within a current time window; a remaining transmission duty-cycle which defines the available duty-cycle during the current time window; and a time offset from the current time when sufficient duty-cycle will become available;
    a communication module configured to control the transceiver to broadcast at least one duty-cycle parameter when transmitting an information packet or when acknowledging receiving an information packet from a neighboring wireless medical device.

2. The wireless medical device according to claim 1, wherein the communication module is configured to control the transceiver to receive at least one duty-cycle parameter from neighboring wireless medical devices.

3. The wireless medical device according to claim 2, further including:
    a duty-cycle management module configured to determine a transmission mode based on at least one of the current duty-cycle, remaining duty-cycle, and time offset parameters of the wireless medical device and of the neighboring wireless medical devices.

4. The wireless medical device according to claim 3, wherein the transmission mode includes:
    a fragmentation mode which fragments the information packet across a plurality of time windows such that the duty-cycle limit is not exceeded in a current time window;
    a modulation mode which adjusts one of frequency and amplitude modulation of the transceiver to reduce a transmission time of the information packet such that the duty-cycle limit is not exceeded in a current time window;
    a compression mode which compresses the information packet to reduce a transmission time of the information packet such that the duty-cycle limit is not exceeded in a current time window;
    a delay mode which delays the transmission of the information packet to a subsequent time window such that the duty-cycle limit is not exceeded in the current time window;
    a retry mode which varies retransmission attempts of unacknowledged packets such that the duty-cycle limit is not exceeded in the current time window;
    an encoding mode which adjusts the coding scheme of the transceiver to encode information in the current time window such that the duty-cycle limit is not exceeded;
    an acknowledgement mode which adjust the acknowledgement policy such that the duty-cycle limit is not exceeded in the current time window;
    a frame aggregation mode which aggregates smaller information packets into a single larger information packet such that the duty-cycle limit is not exceeded in the current time window; and
    a priority mode which transmits higher priority information packets in a current time window and transmits lower priority information in subsequent time windows such that the duty-cycle limit is not exceeded in the current time window.

5. The wireless medical device according to claim 3, wherein the duty-cycle management module is configured to schedule a sleep duration which forces the transceiver into a lower power consumption state until sufficient duty-cycle is available for transmission.

6. The wireless medical device according to claim 3, wherein the duty-cycle management module is configured to adjust a transmission frequency of the wireless transceiver until sufficient duty-cycle is available for transmission.

7. The wireless medical device according to claim 3, wherein an information packet includes at least one of the monitored physiological data, actuator control signals, transmission mode, source address, destination address, frame type, payload, and error correction code.

8. A wireless body area network, comprising:
    a plurality of wireless medical device according to claim 1; and
    a wireless hub configured to interface the plurality of wireless medical device to a medical infrastructure network.

9. The wireless body area network according to claim 8, wherein the wireless hub includes:
    a wireless transceiver configured to receive the monitored physiological data from the at least one wireless medical device and configured to transmit an actuator control signal to control an actuator to deliver therapy, the wireless transceiver having a predetermined duty-cycle limit;

a scheduling module configured to schedule transmissions by the wireless medical devices according to duty-cycle parameters of respective wireless medical devices; and
a control module configured to control the wireless medical devices to transmit and/or receive packets according to scheduled transmissions.

10. A wireless medical device including a processor programmed to perform a method for a body area network, comprising:
creating a wireless body area network which includes a plurality of wireless medical devices according to claim 1 and at least one wireless hub;
interfacing the plurality of wireless medical devices via the wireless hub to a medical infrastructure network;
receiving monitored physiological data from the plurality of wireless medical devices and transmitting an actuator control signal to control an actuator to deliver therapy, the wireless transceiver having a predetermined duty-cycle limit;
scheduling transmissions by the wireless medical devices according to duty-cycle parameters of respective wireless medical devices; and
controlling the wireless medical devices to transmit and/or receive packets according to scheduled transmissions.

11. A non-transitory computer readable medium carrying a computer program which controls one or more processors to perform a method for wirelessly transmitting medical information, comprising:
at least one of a monitoring physiological data of a patient and delivering therapy to the patient;
wirelessly transmitting and/or receiving information packets related to at least one of the monitored physiological data and delivered therapy, the wireless transmission having a duty-cycle limit, the duty-cycle limit represents a maximum transmission on time within a predefined time window;
determining duty-cycle related parameters of the wireless transmission according to the duty-cycle limit, the duty-cycle parameters including at least:
a current transmission duty-cycle which defines the duty-cycle within a current time window,
a remaining transmission duty-cycle which defines the available duty-cycle during the current time window; and
a time offset from the current time when sufficient duty-cycle will become available;
broadcasting at least one duty-cycle parameter when transmitting an information packet or when acknowledging receiving an information packet from a neighboring wireless medical device.

12. The non-transitory computer readable medium according to claim 11, further including:
receiving at least one duty-cycle parameter from neighboring wireless medical devices.

13. The non-transitory computer readable medium according to claim 12, further including:
determining a transmission mode based on at least one of the current duty-cycle, remaining duty-cycle, and time offset parameters of the wireless medical device and of the neighboring wireless medical devices.

14. The non-transitory computer readable medium according to claim 13, wherein the transmission mode includes:

a fragmentation mode which fragments the information packet across a plurality of time windows such that the duty-cycle limit is not exceeded in a current time window;
a modulation mode which adjusts one of frequency and amplitude modulation parameters of the transceiver to reduce a transmission time of the information packet such that the duty-cycle limit is not exceeded in a current time window;
a compression mode which compresses the information packet to reduce a transmission time of the information packet such that the duty-cycle limit is not exceeded in a current time window;
a delay mode which delays the transmission of the information packet to a subsequent time, window such that the duty-cycle limit is not exceeded in the current transmission window;
a retry mode which varies retransmission attempts of unacknowledged packets such that the duty-cycle limit is not exceeded in the current time window;
an encoding mode which adjusts the coding scheme of the transceiver to encode information in the current time window such that the duty-cycle limit is not exceeded;
an acknowledgement mode which adjust the acknowledgement policy such that the duty-cycle limit is not exceeded in the current time window;
an aggregation mode which aggregates smaller information packets into a single larger information packet such that the duty-cycle limit is not exceeded in the current time window; and
a priority mode which transmits higher priority information packets in a current transmission window and transmits lower priority information in subsequent transmission windows such that the duty-cycle limit is not exceeded in the current time window.

15. The non-transitory computer readable medium according to claim 13, further including:
scheduling a sleep duration which forces the transceiver into a lower power consumption state until sufficient duty-cycle is available for transmission.

16. The non-transitory computer readable medium according to claim 13, wherein an information packet includes at least one of the monitored physiological data, actuator control signals, transmission mode, source address, destination address, frame type, payload, and error correction code.

17. The wireless medical device according to claim 1, wherein the duty-cycle limit represents a maximum transmission on time within a predefined time window.

18. A wireless medical device, comprising:
at least one of a sensor which configured to monitor physiological data of a patient and an actuator which delivers therapy to the patient;
a wireless transceiver which configured to transmit and/or receive information packets related to at least one of the monitored physiological data and delivered therapy, the wireless transceiver having a duty-cycle limit, the duty-cycle limit represents a maximum transmission on time within a predefined time window;
at least one processor programmed to:
determine duty-cycle parameters of the wireless transceiver according to the duty-cycle limit, the duty-cycle parameters including at least a current transmission duty-cycle which defines the duty-cycle within a current time window, a remaining transmission duty-cycle which defines the available duty-cycle during the current time window, and a time offset from the current time when sufficient duty cycle will become available;

control the transceiver to broadcast at least one duty-cycle parameter when transmitting an information packet or when acknowledging receiving an information packet from a neighboring wireless medical device;

control the transceiver to receive at least one duty-cycle parameter from neighboring wireless medical devices; and determine a transmission mode based on at least one of the current duty-cycle, remaining duty-cycle, and time offset parameters of the wireless medical device and of the neighboring wireless medical devices.

* * * * *